US010683546B2

(12) United States Patent
Salinas et al.

(10) Patent No.: US 10,683,546 B2
(45) Date of Patent: Jun. 16, 2020

(54) KIT FOR PREDICTING TREATMENT WITH GLUCOCORTICOIDS AND METHOD COMPRISING THE SAME

(71) Applicant: UNIVERSIDAD DE CHILE, Santiago (CL)

(72) Inventors: Cristhian Alejandro Urzua Salinas, Santiago (CL); Irmgadt Annelise Goecke Sariego, Santiago (CL)

(73) Assignee: UNIVERSIDAD DE CHILE (CL)

( * ) Notice: Subject to any disclaimer, the term of this patent is extended or adjusted under 35 U.S.C. 154(b) by 271 days.

(21) Appl. No.: 15/577,093

(22) PCT Filed: May 24, 2016

(86) PCT No.: PCT/CL2016/050025
§ 371 (c)(1),
(2) Date: Nov. 27, 2017

(87) PCT Pub. No.: WO2016/187726
PCT Pub. Date: Dec. 1, 2016

(65) Prior Publication Data
US 2019/0062834 A1    Feb. 28, 2019

(30) Foreign Application Priority Data

May 26, 2015 (CL) .................................. 1420-2015

(51) Int. Cl.
C12P 19/34 (2006.01)
C12Q 1/6883 (2018.01)

(52) U.S. Cl.
CPC ..... C12Q 1/6883 (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 6,762,021 B2 * 7/2004 Tokunaga ................ C12Q 1/26
435/189

FOREIGN PATENT DOCUMENTS

WO    WO03021261 A2    3/2003

OTHER PUBLICATIONS

N_Geneseq_201913 Database entry # ADR27644 (2004) (Year: 2004).*
Rychlik et al., Nucleic Acids Research 17(21), 8543-8551 (1989). (Year: 1989).*
International Search Report; dated Aug. 25, 2016 for PCT Application No. PCT/CL2016/050025.
de Smet, Marc D., and Robert B. Nussenblatt. "Clinical use of cyclosporine in ocular disease." International ophthalmology clinics 33.4 (1993): 31-45.
Sasamoto, Yoichi, Shigeaki Ohno, and Hidehiko Matsuda. "Studies on corticosteroid therapy in Vogt-Koyanagi-Harada disease." Ophthalmologica 201.3 (1990): 162-167.
Rubsamen, Patrick E., and J. Donald M. Gass. "Vogt-Koyanagi-Harada syndrome: clinical course, therapy, and long-term visual outcome." Archives of ophthalmology 109.5 (1991): 682-687.
Leung, Donald YM, et al. "Association of glucocorticoid insensitivity with increased expression of glucocorticoid receptor β." Journal of Experimental Medicine 186.9 (1997): 1567-1574.
Read, Russell W., et al. "Revised diagnostic criteria for Vogt-Koyanagi-Harada disease: report of an international committee on nomenclature." American journal of ophthalmology 131.5 (2001): 647-652.
Melo, Murilo R., et al. "Real-time PCR quantitation of glucocorticoid receptor alpha isoform." BMC molecular biology 5.1 (2004): 19.
Standardization of Uveitis Nomenclature (SUN) Working Group. "Standardization of uveitis nomenclature for reporting clinical data. Results of the First International Workshop." American journal of ophthalmology 140.3 (2005): 509-516.
Goecke, Annelise, and Julia Guerrero. "Glucocorticoid receptor β in acute and chronic inflammatory conditions: clinical implications." Immunobiology 211.1 (2006): 85-96.
Paredes, I., M. Ahmed, and C. S. Foster. "Immunomodulatory therapy for Vogt-Koyanagi-Harada patients as first-line therapy." Ocular immunology and inflammation 14.2 (2006): 87-90.
Gross, Katherine L., and John A. Cidlowski. "Tissue-specific glucocorticoid action: a family affair." Trends in Endocrinology & Metabolism 19.9 (2008): 331-339.
Cobra, Jayme F., et al. "Simultaneous evaluation of in vivo glucocorticoid sensitivity and expression of glucocorticoid receptor alpha-isoform in rheumatoid arthritis patients." Arquivos Brasileiros de Endocrinologia & Metabologia 53.1 (2009): 24-30. Abstract Only.
Ma, Liangliang, et al. "Low expression of glucocorticoid receptor alpha isoform in adult immune thrombocytopenia correlates with glucocorticoid resistance." Annals of hematology 92.7 (2013): 953-960.
Urzua, Cristhian A., et al. "Earlier immunomodulatory treatment is associated with better visual outcomes in a subset of patients with Vogt-Koyanagi-Harada disease." Acta ophthalmologica 93.6 (2015).
Agrawal, Rupesh, et al. "Comparative analysis of anterior chamber flare grading between clinicians with different level of experience and semi-automated laser flare photometry." Ocular immunology and inflammation 24.2 (2016): 184-193.

\* cited by examiner (Continued)

*Primary Examiner* — Kenneth R Horlick
(74) *Attorney, Agent, or Firm* — Mendelsohn & Dunleavy, P.C.

(57) ABSTRACT

An ex vivo method and a kit for predicting the response to a treatment with glucocorticoids (GC) in patients affected by inflammatory diseases, based on quantification of fold change ratio in GR isoform levels.

4 Claims, 2 Drawing Sheets
Specification includes a Sequence Listing.

SEQUENCE LISTING

<160> NUMBER OF SEQ ID NOS: 2

<210> SEQ ID NO 1
<211> LENGTH: 21
<212> TYPE: DNA
<213> ORGANISM: artificial
<220> FEATURE:
<223> OTHER INFORMATION: Synthetic sequence for sense strand PCR primer

<400> SEQUENCE: 1
cctaaggacg gtctgaagag c      21

<210> SEQ ID NO 2
<211> LENGTH: 20
<212> TYPE: DNA
<213> ORGANISM: Artificial
<220> FEATURE:
<223> OTHER INFORMATION: Synthetic sequence for antisense PCR primer

<400> SEQUENCE: 2
gccaagtctt ggccctctat      20

KIT FOR PREDICTING TREATMENT WITH GLUCOCORTICOIDS AND METHOD COMPRISING THE SAME

SPECIFICATION

The present invention refers to the application of an ex vivo method and to a kit for assessing the response to glucocorticoid treatment in patients with autoimmune inflammatory diseases, including uveitis, scleritis, inflammatory bowel disease, arthritis, multiple sclerosis, systemic erythematous lupus, psoriasis, scleroderma or thyroid autoimmune diseases.

Prior Art

Treatment of Intraocular Inflammatory Diseases

Intraocular inflammatory diseases or uveitis are a group of autoimmune pathologies with ocular involvement and, in some cases, with the involvement of other systems, such as the skin or the central nervous system (Read, R. W.; Holland, G.; Rao, N. et al. "Revised diagnostic criteria for Vogt-Koyanagi-Harada disease". Am J Ophthalmol. 131: 647-652, 2001).

The current standard of treatment is the use of glucocorticoids (GC) by systemic route in high doses and, on occasions, for extended periods (Sasamoto, Y.; Ohno, S.; Matsuda, H. "Studies on corticosteroid therapy in Vogt-Koyanagi-Harada disease". Ophthalmologica. 201:162-167, 1990, Rubsamen, P. E.; Gass, D. "Vogt-Koyanagi-Harada Syndrome: clinical course, therapy and long-term visual outcome". Archives of Ophthalmology. 109:682-687, 1991).

The vast majority of patients respond clinically to an early start of GC therapy. However, there is a group of patients (approximately 35%) who are resistant to this therapeutic modality, requiring the use of immunosuppressors (IS) (Paredes, I.; Ahmed, M.; Foster, C. S."Immunomodulatory therapy for Vogt-Koyanagi-Harada patients as first line therapy". Ocular Immunology and Inflammation. 14:87-90, 2006, de Smet, M. D., Nussenblatt, R. B. "Clinical use of cyclosporine in ocular disease". Int. Ophthalmol. Clin. 33:31-45, 1993).

Glucocorticoid Receptor (GR)

The action of GC at the cellular level is determined by the interaction with its intracellular receptor that functions as a ligand dependent transcription factor (Truss, M.; Beato, M. "Steroids hormone receptors interaction with DNA and transcription factors". Endocrine Review. 14:459-78, 1993).

GR is coded in chromosome 5q11-q13 and is made up by 9 exons, exhibiting several transcriptional isoforms synthesized from an alternative splicing process of the primary transcript, the most studied of these being:

Isoform $\alpha$: Constitutes the classic GR that mediates most physiologic effects of GC. It comprises three structural domains, an amino terminus domain containing a trans-activation region, a central domain that constitutes the DNA binding site and a carboxyl terminus end responsible for ligand binding, formed by amino acids 527-777.

Isoform $\beta$: Presents differences at the amino acid sequence level with isoform $\alpha$ in the carboxyl terminus end. Both isoforms are identical as far as the amino acid 727; from this position onwards, isoform $\alpha$ contains 50 amino acids (coded by exon 9$\alpha$), while isoform $\beta$ contains 15 non-homologous amino acids (coded by exon 9$\beta$), resulting in the proteins consisting of 777 and 742 amino acids, respectively. As the carboxyl terminus end contains the GR ligand binding domain, in the case of isoform $\beta$ an inability to bind GC is observed. A negative dominant effect of GR$\beta$ over GR$\alpha$ has also been described, the proposed mechanisms being: competition for DNA binding sites, competition by transcription co-regulators and formation of transcriptionally inactive heterodimers (Goecke, A.; Guerrero, J. "Glucocorticoid receptor $\beta$ in acute and chronic inflammatory conditions: clinical implications". Immunobiology. 211:85-96, 2006, Gross, K. L.; Cidlowski, J. A. "Tissue specific glucocorticoid action: a family affair". Trends in endocrinology and metabolism. 19:331-339, 2008).

Glucocorticoid Resistance

A GC resistance phenomenon has been put forward as a mechanism of a poor clinical response to the treatment with these drugs, in severe inflammatory processes (Leung, D.; Hamid, Q.; Vottero, A. et al. "Association of glucocorticoid insensitivity with increased expression of glucocorticoid receptor beta"; The Journal of Experimental Medicine. 186: 1567-1574, 1997).

Determination of the molecular bases of the mechanism underlying GC resistance is a critical challenge for the development of new therapeutic approaches, particularly in the group of patients where GC constitute the first line therapy, as in intraocular inflammatory diseases.

Among the proposed mechanisms to modify sensitivity to GC, the following are described: mutations in NR3C1 gene that codes for GR (Syndrome of Generalized Resistance to GC), GC metabolism at "pre-receptor level" (catalysed by the enzyme 11$\beta$ hydroxysteroid dehydrogenase), down-regulation in the expression of GR$\alpha$/GR$\beta$ ratio, etc.

The present invention is based on the kinetics of fold change in GR$\alpha$ RNAm levels after the initiation of GC treatment, as an ex vivo method, and on a kit for predicting the early classification of therapy response, i.e., the early identification of patients resistant or non-responsive to GC.

Issues

1. Early selection of an appropriate treatment: A better functional result (better visual acuity) has been described in those patients who initiate their second line therapy (immunosuppressive therapy) at an earlier stage, i.e., in a time frame from 15 days to 1 day, when they have not responded well to the initial GC therapy, an average time of treatment initiation being between 3 and 2, 5 months, compared to patients whose vision gets worse that present a time period of 5.58±1.32 months (Urzua, C. A.; Velasquez, V.; Sabat, P. et al. "Earlier immunomodulatory treatment is associated with better functional outcomes in a subset of patients with Vogt-Koyanagi-Harada disease". Acta Ophthalmologica. Epub ahead of print, 2015).

2) Objective classification of clinical response to treatment: A standardization of the clinical assessment in patients with uveitis, carried out by the group of experts belonging to SUN study group (standardization of Uveitis Nomenclature Study Group) and detailed below, has allowed to describe different schemes for managing these conditions ("The standardization of uveitis nomenclature (SUN) working group. Standardization of Uveitis Nomenclature for reporting clinical data". American Journal of Ophthalmology. 140:509-516, 2005). However, an inter-individual inconsistency has been observed among specialist physicians when consigning parameters of inflammatory activity at eye level, such as the degree of inflammation at the level of the ocular anterior chamber (Agrawal, R.; Keane, P. A.; Singh, J. et al. "Comparative analysis of anterior chamber flare grading between clinicians with different levels of experience and semi-automated laser flare photometry". Ocular Immunology and Inflammation. Epub ahead of print, 2015). There is also a group of patients where it is not possible to make a full clinical assessment, such as in those subjects with a mature cataract, corneal opacities, among others.

DETAILED DESCRIPTION OF THE INVENTION

Figure 1:
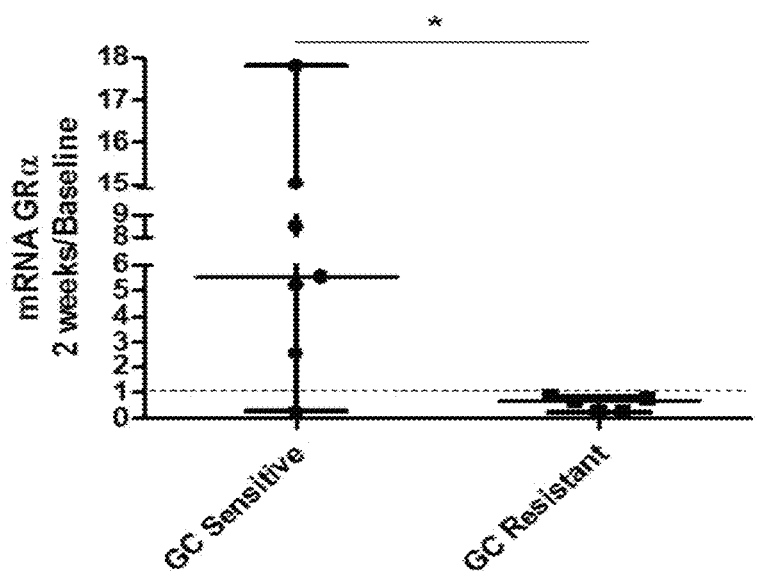
FIG. 1: shows fold change ratio of GRα expression transcripts after two weeks of treatment, in PBMC of patients with Vogt-Koyanagi-Harada (VKH) disease, depending on the clinical sensitivity to GC therapy. The fold change ratio of GRα levels was assessed in PBMC of patients with VKH two weeks after a prednisone treatment, according to the clinical response to GC therapy. Mann Whitney Test. *p<0.05.
Figure 2:
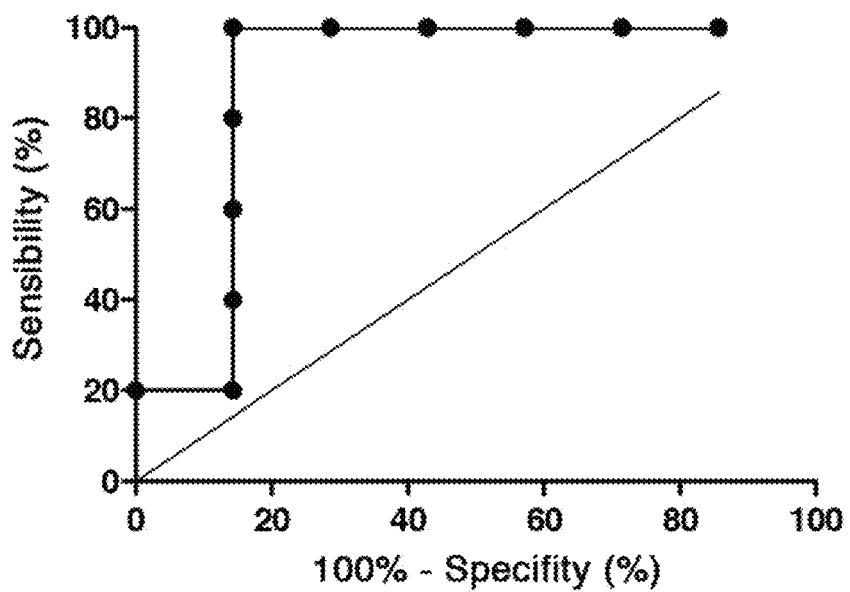
FIG. 2: Shows ROC curve (AUC).
Figure 3:
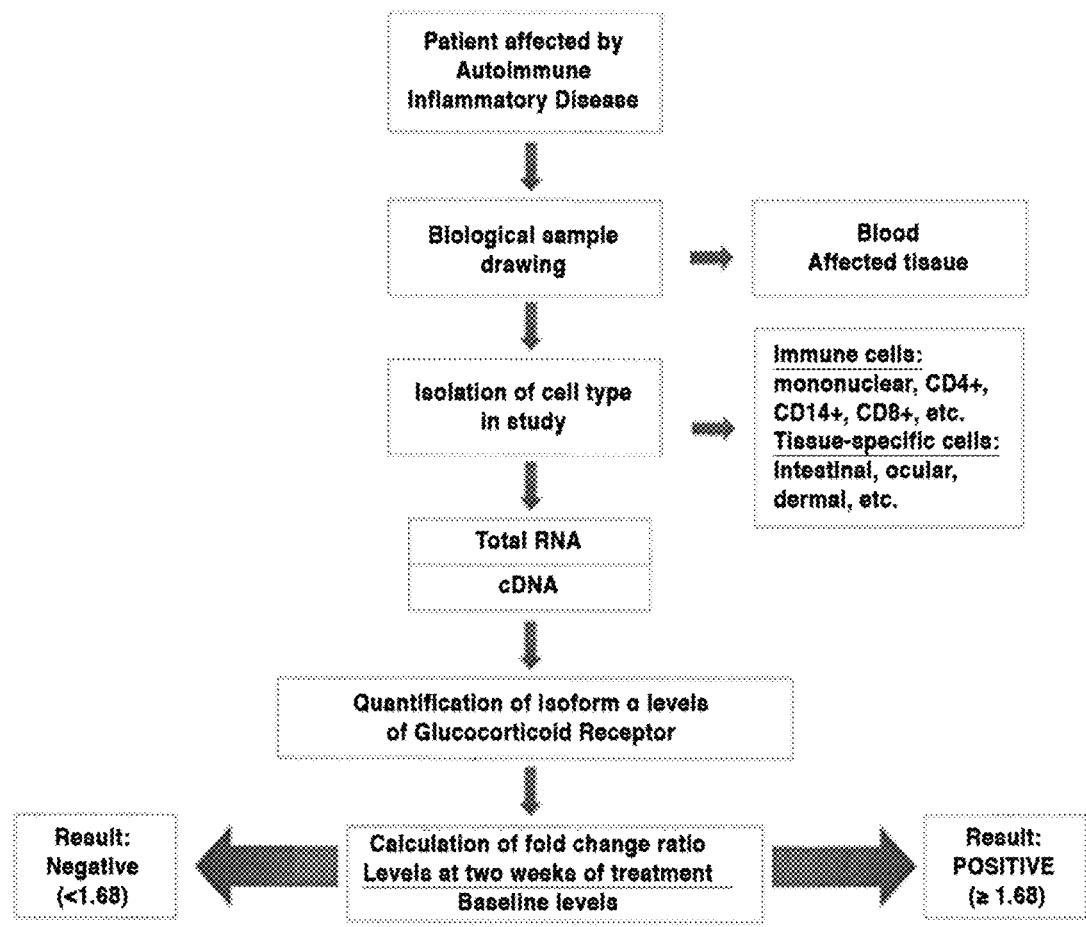
FIG. 3: Shows a flow diagram of the present ex vivo method.

The present invention refers to the application of an ex vivo method to assess the response to treatment in patients with autoimmune inflammatory diseases.

The ex vivo method is conducted within a protocol that comprises various sequential steps:

1) Obtainment of a 10-100 ml blood sample—preferably collected in the morning by automatic aspiration (vacutainer®) or manual (disposable syringe) methods. As an alternative or complementarily, the affected tissue or cell type may be completely or partially removed in order to carry out measurements.

2) After obtaining the sample, peripheral mononuclear cells (PBMC) are procured by the Ficoll gradient method, where a hydrophilic polysaccharide allows separating blood components into plasma, PBMC and erythrocytes. Alternatively or complementarily, the isolation of specific cell sub-types, such as CD4+, CD14+, CD8+cells, among others, may be conducted using a strategy based on magnetic microbeads or cell sorting by flow cytometry.

3) Subsequently, total RNA is extracted (Life Technologies, Inc.) by the TRIZOL method. For the obtainment of cDNA, 0.5 to 2 μg RNA is used as a template. Reverse transcription is performed preferably with kit ImProm-II™ Reverse Transcription System (Promega): a reaction mixture is prepared with 0.5 to 2 μg RNA, 1 μL Random Hexamers, 4 μL 5× ImProm-II™ RT buffer up to a final 20 μL volume, which is then incubated at 70° C. for 5 minutes, 4° C. for 5 minutes, 25° C. for 5 minutes, 42° C. for 60 minutes and 25° C. for 5 minutes.

4) cDNA is amplified using primers specific for GRα isoform: 5'-CCTAAGGACGGTCTGAAGAGC-3' (sense, SEQ ID NO: 1) and 5'-GCCAAGTCTTGGCCCTCTAT-3' (antisense, SEQ ID NO: 2) that correspond to nucleotides 2158-2178 and 2616-2635 of GRα cDNA.

5) For the amplification, a cDNA polymerase is used, preferably, the enzyme Go Taq® Flexi DNA Polymerase (Promega), starting the reaction with an initial 5 minute incubation at 95° C., followed then by 30 cycles as detailed: 95° C. for 30 seconds, 60° C. for 30 seconds and 72° C. for 30 seconds. For quantification by Real-Time qPCR a fluorophore is used, using preferably SYBR Green as fluorophore. GR measurements are made in duplicate. Finally, the results are standardized according to the expression of 18s rDNA gene that codes for the 18s ribosomal subunit.

6) Repetition of GRα mRNA level assessment according to the described protocol is carried out two weeks after initiating GC treatment. An increase is observed in GRα expression in sensitive patients and a reduction of the same in resistant patients (median of 5.5 versus 0.7, respectively).

7) Calculation of fold change ratio in GRα mRNA levels between the initial assessment and a later assessment after 2 weeks of GC treatment.

GR fold change ratio=GR mRNA-2 weeks/GR mRNA at baseline

8) Assignment of the results: levels of GRα mRNA fold change ratio in the range from 1.00 to 17.8 constitute a POSITIVE sensitivity result or a good response to GC. Preferably, levels of GRα mRNA fold change ratio in the range from 1.00 to 5.36 constitute a POSITIVE sensitivity result or a good response to GC. Values below these ranges constitute a NEGATIVE sensitivity result or a bad response to GC.

Another object of the present invention refers to a kit for predicting the response to a GC treatment in patients with an inflammatory disease, said kit comprising:

means for obtaining a biological sample from the patient; preferably, automatic or manual aspiration means including in the latter case, for example, a disposable syringe. The biological sample from the patient may be of blood, of cells involved in the immune response or of the specific cell types affected by the disease.

means for obtaining from the sample, by Ficoll gradient method, peripheral mononuclear cells (PBMC), which include a hydrophilic polysaccharide that separates plasma, PBMC and erythrocytes, or alternatively or complementarily, magnetic microbeads or cell sorting that allow to isolate, by flow cytometry, specific cell subtypes including among others, CD4+, CD14+CD8+ cells;

means for extracting total RNA from the PBMC and obtain cDNA from the ARN template, that include a kit for carrying out reverse transcription;

primers for cDNA amplification that comprise 5'-CCTAAGGACGGTCTGAAGAGC-3' (sense, SEQ ID NO. 1) and 5'-GCCAAGTCTTGGCCCTCTAT-3' (antisense, SEQ ID NO: 2), and correspond to nucleotides 2158-2178 and 2616-2635 of GRα cDNA, and DNA polymerase;

means for quantifying the expression of GR isoforms in said biologic sample from the patient, which include a fluorophore and instructions for standardizing the results according to the expression of the 18s rDNA gene that codes for the 18s ribosomal subunit;

instructions for calculating the fold change ratio in GRα mRNA levels, between the initial assessment and the assessment after a period of time from 1 to 180 days.

instructions for assigning results from the fold change ratio in GRα mRNA levels: values in the range from 1.00 to 17.8 constitute a result of sensitivity to GC or of a good response to GC, while values below said range indicate resistance to GC. Preferably, the values obtained in a range from 1.00 to 5.36 constitute a POSITIVE sensitivity result or a good response to GC, while the values below said range indicate a NEGATIVE sensitivity result or a bad response to GC.

Example of Application: Pilot Study in Patients with Vogt-Koyanagi-Harada Disease The method described in the present invention has been assessed in a group of 21 patients with Vogt-Koyanagi-Harada (VKH) disease, a specific uveitis subtype.

A cohort study has been conducted on 21 patients with VKH disease, defined with the following criteria:

Cases: 13 patients affected by VKH with an inadequate response to oral treatment with 1 mg/Kg/day prednisone, in two separate doses, ⅔ of the daily dose in the morning and ⅓ of the dose in the afternoon.

Controls: 8 patients affected by VKH with an adequate response to the oral treatment with 1 mg/Kg/day prednisone, in two separate doses, ⅔ of the daily dose in the morning and ⅓ of the dose in the afternoon.

Inadequate Response Criteria
Use of a known and approved immunosuppressive therapy during the acute stage of the disease.
Indication of an immunosuppressive therapy in the context of the absence of adverse side effects with the use of GC, associated to one or more of the following criteria:
Persistence of Retinal Detachment for a time longer than 6 weeks.
Absence of clinical improvement of the inflammatory activity, or persistence of inflammation for a time longer than 6 weeks, defined under Standardization of Uveitis Nomenclature for reporting clinical data consensus (The standardization of uveitis nomenclature (SUN) working group. Standardization of Uveitis Nomenclature for reporting clinical data". American Journal of Ophthalmology. 140:509-516, 2005):
Reduction of the inflammation in two levels (in the anterior chamber or vitreous)
Reduction of the inflammation to grade 0 (in the anterior chamber or vitreous).

In this respect, the amount of intraocular inflammation is quantified using a biomicroscope and making an assessment by indirect ophthalmoscopy, establishing the following levels:

Anterior Chamber:
Grade 0=without cells
Grade 0.5=1-4 cells per mm$^2$,
Grade 1=5-15 cells per mm$^2$,
Grade 2=16-25 cells per mm$^2$,
Grade 3=26-50 cells per mm$^2$,
Grade 4=>50 cells per mm$^2$,
Vitreous
Grade 0=Without vitreous opacity
Grade 1=Minimal vitreous opacity, posterior pole clearly visible.
Grade 2=Mild vitreous opacity, slightly blurred posterior pole details.
Grade 3=Medium vitreous opacity, highly blurred posterior pole details.
Grade 4=Pronounced vitreous opacity, posterior pole details not visible.

An analysis was conducted on the fold change ratio of GR transcript expression two weeks after treatment initiation, in comparison with baseline levels (prior to treatment initiation), segregating in accordance with the clinical response during follow-up. To calculate this fold change ratio, an arithmetic operation is conducted, that consists in dividing the GR levels obtained two weeks after the treatment and the baseline or initial GR levels.

$$GR\ fold\ change\ ratio = GR\ mRNA\text{-}2\ weeks/GR\ mRNA\ at\ baseline$$

TABLE 1

Fold change ratio of GR levels in PBMC of patients with Vogt-Koyanagi-Harada disease, after two weeks of Prednisone treatment
Clinical Sensitivity to GC[1]

| Sensitive | Resistant |
|---|---|
| 15 | 0.841 |
| 5.52 | 0.759 |
| 5.21 | 0.667 |
| 8.49 | 0.225 |
| 2.53 | 0.243 |
| 0.237 | |
| 17.8 | |

[1]GC = Glucocorticoids

As shown in FIG. 1, after two weeks of systemic therapy with GC, an increase is produced in GRα mRNA levels in patients who are clinically sensitive to GC (fold change median=5.5; range=0.23-17.8), while in resistant patients, a reduction of GRα levels is observed (fold change median=0.7; range=0.22-0.84), this difference being statistically significant ($p=0.03$).

To assess the yield of fold change ratio in the expression of GRα as an ex vivo prediction method, the area below the curve (AUC) of ROC was calculated, and a range of appropriate values between 1.00 and 5.36 was identified from it to classify treatment response. Particularly with a cut-off point of 1.68, sensitivities of 100% (46.2-100) specificities of 85-7% (42-99.2), positive predictive values of 83.3% (36.4-99.1) and negative predictive values of 100% (51.6-100) were obtained, see Table 2

TABLE 2

Assessment of diagnostic yield of different cut-off points of GRα fold change ratio for identifying GC treatment response in patients with VKH.

| Cut-off Point | Sensitivity % (IC 95%) | Specificity % (IC 95%) |
|---|---|---|
| <0.2310 | 20.00 (0.50-71.64) | 100.0 (59.04-100.0) |
| <0.2400 | 20.00 (0.50-71.64) | 85.71 (42.13-99.64) |
| <0.4550 | 40-00 (5.27-85.34) | 85.71 (42.13-99.64) |
| <0.7130 | 60.00 (14.66-94.73) | 85.71 (42.13-99.64) |
| <0.8000 | 80.00 (28.36-99.49 | 85.71 (42.13-99.64) |
| <1.686 | 100.0 (47.82-100.0) | 85.71 (42.13-99.64) |
| <3.870 | 100.0 (47.82-100.0) | 71.43 (29.04-96.33) |
| <5.365 | 100.0 (47.82-100.0) | 57.14 (18.41-90.10) |
| <7.005 | 100.0 (47.82-100.0) | 42.86 (9.89-81.59) |
| <11.75 | 100.0 (47.82-100.0) | 28.57 (3.66-70.96) |
| <16.40 | 100.0 (47.82-100.0) | 14.29 (0.36-57.87) |

The invention claimed is:

1. An ex vivo method for predicting treatment response after a period of time between 1-180 days of glucocorticoid (GC) treatment, which is at an early stage in a patient affected by an autoimmune inflammatory disease, comprising steps of:
  a) obtaining a biological sample from a patient, by automatic or manual aspiration methods, wherein said biological sample is selected from blood, tissue or cells from said patient that are totally or partially affected by said disease or a combination of the blood sample and the tissue or cell sample from said patient;
  b) obtaining from the biological sample, peripheral mononuclear cells (PBMC) by the Ficoll gradient method, CD4+cells, CD14+cells, CD8+cells, or a combination thereof by a magnetic separation method or cell sorting by flow cytometry, and/or cells from the affected tissue;
  c) extracting total RNA from the isolated cells obtained from the biological sample and obtaining cDNA using said RNA as a template by conducting a reverse transcription reaction including use of a kit for carrying out said reverse transcription reaction;
  d) amplifying the cDNA obtained in step (c), using primers that are specific for a GRα isoform: 5'-CCTAAGGACGGTCTGAAGAGC-3' (sense, SEQ ID NO: 1) and 5'-GCCAAGTCTTGGCCCTCTAT-3' (antisense, SEQ ID NO:2) that correspond to nucleotides 2158-2178 and 2616-2635 of GRα cDNA;
  e) quantifying levels of expression of GR isoforms by real time qPCR using a fluorophore, carrying out GRα measurements in duplicate to obtain GRα mRNA expression levels, and standardizing said GRα mRNA expression levels against expression levels of a 18S rDNA gene that codes for ribosomal subunit 18s;
  f) repeating the steps (a)-(e) in a sample taken between 1-180 days after initiation of the GC treatment; and
  g) calculating a fold change ratio of said standardized GRα mRNA levels between the first step (e) and the second step (e) conducted between 1-180 days after initiation of the GC treatment, wherein values of said fold change ratio from 1.00 to 17.8 indicate that the patient is sensitive to GC treatment, while values of said fold change ratio below 1 indicates that the patient is resistant to GC.

2. The ex vivo method according to claim 1, wherein values of said fold change ration n normalized GRα mRNA levels of from 1.00 to 5.36 indicate that the patient is sensitive to GC treatment.

3. The ex vivo method according to claim 1, wherein the autoimmune inflammatory disease is selected from the group consisting of uveitis, scleritis, inflammatory bowel disease, arthritis, multiple sclerosis, systemic erythematous lupus, psoriasis, scleroderma and thyroid autoimmune diseases.

4. The ex vivo method according to claim 2, wherein the autoimmune inflammatory disease is selected from the group consisting of uveitis, scleritis, inflammatory bowel disease, arthritis, multiple sclerosis, systemic erythematous lupus, psoriasis, scleroderma and thyroid autoimmune diseases.

* * * * *